(12) United States Patent
Keusenkothen

(10) Patent No.: US 11,254,882 B2
(45) Date of Patent: Feb. 22, 2022

(54) CONVERSION OF C2 HYDROCARBONS IN THE PRESENCE OF METHANE

(71) Applicant: ExxonMobil Chemical Patents Inc., Baytown, TX (US)

(72) Inventor: Paul F. Keusenkothen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/967,230

(22) PCT Filed: Jan. 18, 2019

(86) PCT No.: PCT/US2019/014263
§ 371 (c)(1),
(2) Date: Aug. 4, 2020

(87) PCT Pub. No.: WO2019/164610
PCT Pub. Date: Aug. 29, 2019

(65) Prior Publication Data
US 2021/0032549 A1 Feb. 4, 2021

Related U.S. Application Data

(60) Provisional application No. 62/633,261, filed on Feb. 21, 2018.

(30) Foreign Application Priority Data

Apr. 19, 2018 (EP) .................................. 18168135

(51) Int. Cl.
| | | |
|---|---|---|
| *C10G 50/00* | (2006.01) | |
| *B01J 19/24* | (2006.01) | |
| *B01J 29/48* | (2006.01) | |
| *C07C 2/76* | (2006.01) | |
| *C07C 2/42* | (2006.01) | |
| *C07C 4/06* | (2006.01) | |

(52) U.S. Cl.
CPC ............ *C10G 50/00* (2013.01); *B01J 19/245* (2013.01); *B01J 29/48* (2013.01); *C07C 2/42* (2013.01);
(Continued)

(58) Field of Classification Search
CPC ............ C10G 50/00; C10G 2300/4018; C10G 2400/30; C10G 2300/1025; C07C 2/76;
(Continued)

(56) References Cited

U.S. PATENT DOCUMENTS 7,176,342 B2  2/2007 Bellussi et al.
8,278,237 B2  10/2012 Yamada et al.
(Continued)

FOREIGN PATENT DOCUMENTS

WO  2010/069582 A1  6/2010

OTHER PUBLICATIONS

Aboul-Gheit et al. ("Molybdenum substitution by copper or zinc in H-ZSM-5 zeolite for catalyzing the direct conversion of natural gas to petrochemicals under non-oxidative conditions", Fuel 90 (2011) 3040-3046). (Year: 2011).*

*Primary Examiner* — Ali Z Fadhel

(57) ABSTRACT

A catalyst and corresponding methods of using a catalyst are provided that can be beneficial for conversion of paraffins into a product stream enriched in aromatics and/or methane while reducing or minimizing the content of ethane in the product stream. Such catalysts and methods can be useful, for example, for processing a raw gas, associated gas, tail gas, natural gas, or other type of methane-containing feed stream to convert $C_{2+}$ hydrocarbons in the stream to heavier hydrocarbons and methane while reducing or minimizing content of ethane in the products from the conversion reaction. Such conversion can be useful for upgrading a methane-containing feed stream to have an energy content (Continued)

that is suitable for pipeline transport under one or more specifications for transport of natural gas. The catalyst and corresponding method can also be beneficial when used as a second stage catalyst in a configuration involving multiple conversion stages.

23 Claims, 5 Drawing Sheets

(52) U.S. Cl.
CPC ............... *C07C 2/76* (2013.01); *C07C 4/06* (2013.01); *B01J 2219/0004* (2013.01); *C10G 2300/4018* (2013.01); *C10G 2400/30* (2013.01)

(58) Field of Classification Search
CPC .. C07C 2/42; C07C 4/06; B01J 19/245; B01J 29/48; B01J 2219/0004
See application file for complete search history.

(56) References Cited

U.S. PATENT DOCUMENTS

| | | | |
|---|---|---|---|
| 8,558,045 B2 | 10/2013 | Yamada et al. | |
| 8,835,706 B2 * | 9/2014 | Iyer | C07C 2/76 585/412 |
| 2017/0087540 A1 | 3/2017 | Ilias et al. | |
| 2017/0088484 A1 | 3/2017 | Maher et al. | |
| 2017/0088487 A1 | 3/2017 | Buchanan et al. | |

* cited by examiner

CONVERSION OF C2 HYDROCARBONS IN THE PRESENCE OF METHANE

CROSS-REFERENCE TO RELATED APPLICATIONS

This application is a U.S. national phase application of PCT application No. PCT/US2019/014263 having a filing date of Jan. 18, 2019, which claims priority to and the benefit of U.S. provisional application Ser. No. 62/633,261 having a filing date of Feb. 21, 2018, the contents of both of which are incorporated by reference in their entirety.

FIELD

This invention relates to reactors, associated reactor systems, methods, catalysts, and processes for conversion of paraffin-containing streams to aromatics while reducing or minimizing ethane content.

BACKGROUND

Oil extraction sites for withdrawal of petroleum from a mineral reservoir can typically produce a mixture of gas and liquid phase products. The liquid phase products from the mineral reservoir can typically be stored in tanks and/or diverted into a pipeline system to allow for further processing at a central location. While the liquid phase petroleum product is often the primary desired target, the gas phase product (such as raw natural gas) can also include substantial carbon content. Additionally, at some extraction sites, the gas phase product can correspond to the primary or intended product from the extraction site.

Unfortunately, transportation of gas phase products generated at an extraction site can present substantial difficulties which may make it cost prohibitive to attempt to transport the gas phase products (or at least portions of the gas phase products) for further processing. For example, natural gas is a commonly pipelined product, with various specifications controlling the content of the natural gas depending on the pipeline. Many pipeline specifications have limits on the heat content of natural gas in order to avoid condensation of liquids in the pipeline. As a practical matter, such specifications correspond to limits on the amount of $C_{2+}$ hydrocarbons that can be present in a natural gas stream. For natural gas streams that have a sufficiently high methane content, the natural gas stream may have an energy content that is suitable for pipeline transport after removal of non-hydrocarbon impurities. However, for "rich" natural gas streams that contain a sufficiently high content of $C_{2+}$ hydrocarbons, additional processing steps may be needed before the natural gas stream can be transported via pipeline.

Some conventional options for reducing the content of $C_{2+}$ hydrocarbons in a natural gas stream can involve converting at least a portion of the $C_{2+}$ hydrocarbons into other products, such as aromatic products. U.S. Pat. No. 7,176,342 While such methods can be at least partially effective, conventional methods for conversion of $C_{2+}$ hydrocarbons to aromatics often have limited conversion rates for conversion of ethane.

Other conventional options for reducing the content of $C_{2+}$ hydrocarbons in a natural gas stream can involve separation of the natural gas stream to form a stream containing a majority of the methane and one or more other streams containing a majority of the $C_{2+}$ hydrocarbons. While such separation methods can be at least partially effective, a problem can remain in how to dispose of the $C_{2+}$ hydrocarbons. For separation products such as propane, a large consumer marketplace is available for sale of propane for a variety of uses. Unfortunately, the uses for commercial quantities of ethane are more limited, any many extraction sites may not have access to an application that can consume ethane that is separated from natural gas at the extraction site. While $C_{2+}$ hydrocarbons can be flared, flaring is an extremely low value use as this corresponds to a waste of the energy content of the hydrocarbons. Flaring is also limited by regulation in some locations.

As natural gas continues to grow in importance as a product from various extraction sites, it would be beneficial to have additional systems and/or methods that can allow for processing of natural gas fractions in a manner that effectively utilizes a high percentage of the carbon from the extraction site while reducing or minimizing the amount of ethane.

For example, International Publication Number WO/2010/069582 describes a process for conversion of methane into hydrogenated liquid hydrocarbons. An example of a suitable catalyst for the conversion is described as a H-ZSM-5 zeolite having an $SiO_2/Al_2O_3$ molar ratio of 20 to 100, about 0.5 wt. % to 15 wt. % of Mo supported on the catalyst, and 0.1 wt. % to 5 wt. % of Ce supported on the catalyst.

As another example, U.S. Pat. Nos. 8,278,237 and 8,558,045, describe catalysts and corresponding methods for conversion of non-aromatic hydrocarbon compounds into aromatic products such as benzene, toluene, and xylene. The catalysts for the conversion comprise molecular sieve and metal such as Mo.

In order to decrease the amount of $C_{2+}$ hydrocarbon and increase the amount of aromatics, U.S. Patent Application Publication No. US2017-0088484 discloses separating (i) methane and ethane and (ii) a $C_{2+}$ raffinate from a hydrocarbon stream such as natural gas that may be too rich in $C_{2+}$ hydrocarbon for transportation via pipeline. The separated methane-ethane stream is sufficiently lean in ethane for pipeline transportation. The $C_{2+}$ raffinate is converted to aromatics in the presence of a catalyst comprising molecular sieve and metal such as Mo.

More efficient processes and methods are desired for upgrading light hydrocarbon streams. In particular, methods and processes are desired that do not need to remove methane and/or ethane from the light hydrocarbon stream before catalytic processing.

SUMMARY OF THE INVENTION

In various aspects, the invention the conversion of a feed containing methane and ethane, such as natural gas feeds, to a products having greater concentrations of methane than the feed, but a lesser concentration of ethane. The conversion is carried out in the presence of at least one catalyst comprising (i) at least one medium pore zeolitic framework structure material, and (ii) 0.1 wt. % to 10 wt. % of Zn and one or more of Mo, Pt, and Fe.

The catalysts and corresponding processes and methods can allow for production of heavier hydrocarbons, such as aromatics, from light alkanes while also reducing or minimizing the ethane content of the resulting conversion effluent. The conversion effluent is sufficiently rich in methane and sufficiently lean in ethylene to be suitable for pipeline transportation, which can obviate the need for separating methane and ethane upstream of the catalytic processing.

In some aspects, additional benefits can be achieved by converting a natural gas stream (or other methane-containing feed) in a plurality of catalytic stages. In such aspects, a first stage can include conventional catalysts and processes for conversion to aromatics of a stream comprising methane, ethane and $C_{3+}$ aromatics. The first stage converts a majority of the $C_{3+}$ hydrocarbons to aromatics and $C_2$ hydrocarbon, resulting an effluent containing aromatics, $C_2$ hydrocarbon, and methane. Effluent from the first stage is conducted to a second stage for conversion of the effluent's $C_2$ hydrocarbon. Unlike prior art processes, such as those described in U.S. Patent Application Publication No. 20170088484, the second stage's catalyst and operating conditions favor selectivity for methane over selectivity for aromatics.

DETAILED DESCRIPTION

Figure 1:
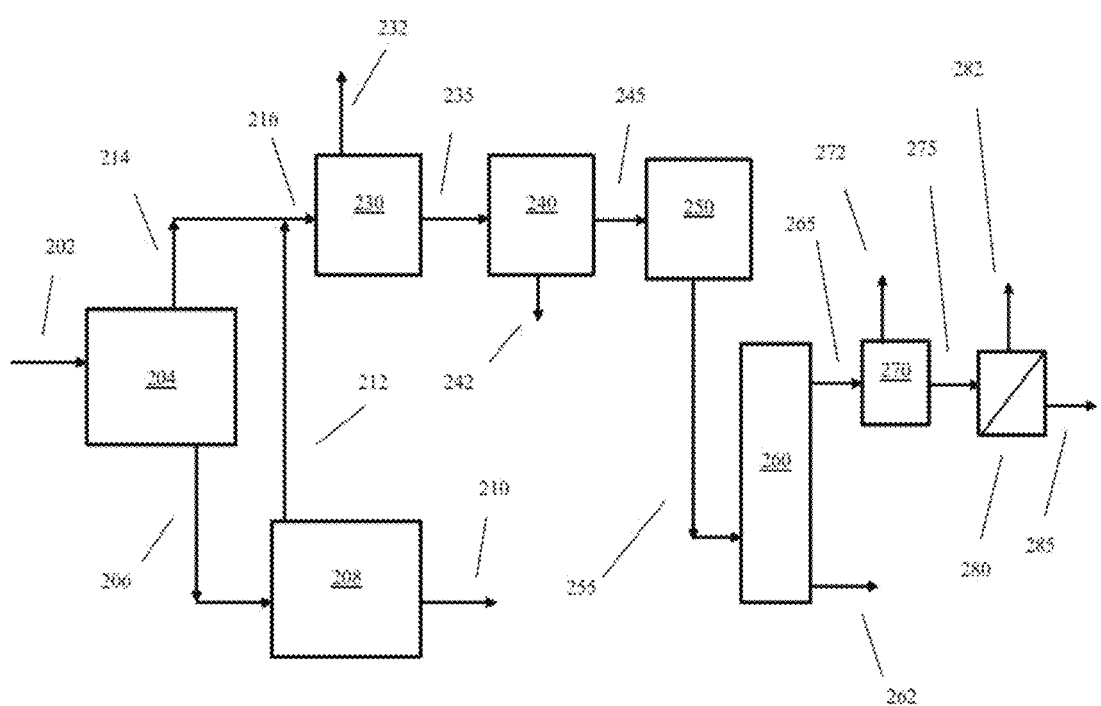
FIG. 1 shows a process flow for processing gas phase products from an extraction site.

In various aspects, catalysts, methods, and processes are provided that can be beneficial for conversion of a feed comprising paraffin, particularly light hydrocarbon compounds (e.g., $C_{5-}$ or $C_{4-}$ or $C_{3-}$, or $C_{2-}$ hydrocarbon compounds) as may be present in a tail gas or other natural gas stream. The conversion produces a product stream that is richer in aromatics and/or methane but leaner in ethane in comparison with the feed. Such catalysts, processes, and methods can be useful, for example, for processing a raw gas, associated gas, tail gas, natural gas, or other type of methane-containing feed to convert $C_{3+}$ hydrocarbons in the stream to heavier (generally $C_{5+}$) hydrocarbon compounds and methane while converting $C_2$ hydrocarbon compounds in the feed with a greater selectivity to methane and a lesser selectivity to $C_{5+}$ hydrocarbon (and in particular a lesser selectivity to aromatics) than is the case in the $C_{3+}$ conversion Such processes and methods are desirable for (i) upgrading a methane-containing feed stream to have an energy content that is suitable for pipeline transport under one or more specifications for transport of natural gas, and/or (ii) producing heavier hydrocarbon products of greater value while still providing beneficial uses for an increased or maximized portion of the carbon (particularly carbon in the form of hydrocarbon) in the methane-containing feed.

In some aspects, the processing can correspond to multi-stage processing. In such aspects, a first processing stage can convert a majority of the $C_{3+}$ components of the methane-containing feed to heavier hydrocarbons. The resulting first stage effluent can then be processed in a second processing stage that includes a catalyst as described herein. The second processing stage can provide additional conversion of ethane (and optionally at least a portion of any $C_{3+}$ hydrocarbon in the effluent from the first stage). The second stage conversion operates using a catalyst and process conditions for the selective conversion of ethane to methane, and optionally with selectivity for producing additional $C_{5+}$ hydrocarbon (e.g., additional aromatics) in order to decrease or minimize the ethane content in the second stage effluent.

Natural gas recovered at a well-head (either associated gas or non-associated gas) usually contains impurities and contaminants including water vapor, hydrogen sulfide, carbon dioxide, nitrogen, and other compounds. Various techniques for sulfur removal, acid gas removal, and/or water removal can be used to remove at least a portion of the impurities from the gas stream. Depending on the extraction source or reservoir, the natural gas may correspond to a "rich" natural gas that includes several wt. % or more of various $C_{2+}$ hydrocarbons. If the quantity of $C_{2+}$ hydrocarbons is sufficiently large, the energy content of the gas may be greater than a heating value of 42.0 $MJ/sm^3$, or greater than a heating value of 41.5 $MJ/sm^3$. Such an elevated energy content for a natural gas may be greater than a pipeline specification for transport of the gas. In order to transport such a "rich" natural gas by pipeline, the energy content of the natural gas needs to be reduced, such as by removal of at least a portion of the $C_{2+}$ hydrocarbons in the natural gas. More generally, typical specifications for many gas pipelines can include, for example, ≤12 wt. % ethane, ≤5 wt. % propane, ≤2 wt. % butanes, a Wobbe Index of from 49.01 $MJ/sm^3$ to 52.22 $MJ/sm^3$, and a heating value of from 36.07 $MJ/sm^3$ to 41.40 $MJ/sm^3$.

Conventionally, one option for reducing the $C_{2+}$ content of a methane-containing stream can be to convert a portion of the stream to heavier hydrocarbons, such as $C_{6+}$ aromatics or other $C_{6+}$ compounds. See, e.g., U.S. Patent Application Publication No. 2017-0088482 which is incorporated by reference herein in its entirety. These heavier hydrocarbons can then be separated from the light gases ($C_{3-}$) in the conversion effluent by any convenient method, such as distillation. Unfortunately, the single-pass conversion rates of typical conversion catalysts for ethane are relatively low, resulting in conversion of only a few percent of the ethane in the feed. In addition to having a low ethane conversion rate, many conversion catalysts can also generate small amounts of ethane under the conversion conditions. This can cause the net conversion of ethane to be reduced or minimized for a conventional conversion catalyst, possibly corresponding to no net conversion under some conditions. As a result, even after performing conversion on a methane-containing gas stream and subsequently removing the heavy hydrocarbons, the remaining portion of the conversion effluent can still include an undesirably high content of ethane. This undesirably high content of ethane can cause the remaining portion of the conversion effluent to still have an energy content that is greater than a target value based on a pipeline specification, even after a second stage for ethane aromatization. Consequently, an additional separation of ethane from methane may be required in order to form a gas stream that is suitable for pipeline transport. Such separations typically use equipment that may not be available at natural gas production sites.

The prior art discloses aromatizing $C_{2+}$ hydrocarbon using catalysts comprising molecular sieve and one or metals selected from groups 3-13 of the Periodic Table. It has been unexpectedly discovered that among these there are certain combinations of molecular sieve and metals exhibiting a conversion of $C_2$ hydrocarbon in feeds comprising methane and $C_2$ hydrocarbon, but with a greatly decreased selectivity to aromatics and a greatly increased selectivity to methane in comparison with the prior art processes. Surprisingly, this has been found to be the case even when the feed further comprises one or more of substantially-saturated $C_{3+}$ hydrocarbon, aromatics, and molecular hydrogen. Even more surprisingly, particularly in view of Le Chatelier's Principle, this has been found to be the case even when the feed comprises a major amount of methane, e.g., ≥60 mole % of methane, or ≥70 mole, such as in the range of from 50 mole % to 90 mole % of methane per mole of the feed. The suitable catalyst can include a zeolitic framework and can further include a combination of supported metals on the catalyst. In some aspects, the supported metals can correspond to a combination of Zn and Mo. Additionally or alternatively, the supported metals can correspond to a combination of Zn with one or more of Mo, Pt, and Fe. In some aspects, the zeolitic framework can correspond to an MFI framework (ZSM-5). Additionally or alternatively, the zeolitic framework can correspond to a catalyst having the framework type of ZSM-5, ZSM-11, ZSM-12, ZSM-22, ZSM-23, ZSM-35, ZSM-48, including and mixtures and intermediates thereof.

When a feed containing both methane and $C_{2+}$ hydrocarbons is exposed to a catalyst including a zeolitic framework and the specified combination of metals, conversion of the $C_{2+}$ hydrocarbons can occur with increased selectivity to methane but without an undesirable amount of conversion of $C_{3+}$ hydrocarbon as may be present in the feed. The amount of $C_{6+}$ hydrocarbons generated during conversion may be greater than, similar to, or less than the amount of $C_{6+}$ hydrocarbons that would be produced by a conventional conversion catalyst, but is typically less than. However, in spite of the potentially similar or even reduced activity for production of $C_{6+}$ products, the catalysts described herein can have increased activity for net conversion of ethane with a desirable increase in selectivity to methane. By converting additional ethane into methane and/or $C_{6+}$ hydrocarbons, and/or by decreasing or minimizing production of ethane in the conversion reaction, the catalysts described herein can generate a conversion product having a decreased or minimized amount of ethane content, and especially a lesser concentration of ethane in the conversion product compared to that of the feed. This can be beneficial for various reasons. To the degree that decreasing ethane concentration in the products corresponds to an increase in methane, this is beneficial based on the desire to produce a methane-containing stream (i.e., natural gas) that has a suitable energy content for pipeline transport. To the degree that the reduction in ethane in the products corresponds to an increase in $C_{6+}$ products, this is beneficial based on the desire to produce heavier hydrocarbons, which typically have a higher value. It is noted that the catalysts described herein have comparable net activity relative to conventional catalysts for conversion of $C_3$ and $C_4$ hydrocarbons.

In various aspects, a molar ratio of ethane or, more generally $C_2$ hydrocarbon compounds, in a converted product stream to ethane or $C_2$ hydrocarbons in the feed stream (to the conversion reaction) can be 0.8 or less, or 0.7 or less, or 0.6 or less, or 0.4 or less, or 0.2 or less, or possibly still lower. The molar ratio of $C_2$ hydrocarbons in the converted product versus the feed can represent the amount of net conversion of $C_2$ hydrocarbons that occurs during the conversion reaction. It is noted that some ethane may be dehydrogenated to ethene under conversion conditions. Thus, a feed containing methane and ethane may result in a product stream including methane and both ethane and ethene. Additionally or alternatively, in various aspects a molar ratio of methane ($C_1$ hydrocarbon) in a converted product stream to methane ($C_1$ hydrocarbon) in the feed stream to the conversion reaction can be 1.4 or more, or 1.5 or more, or 1.6 or more, such as up to 1.8 or possibly still higher. This can represent the additional methane generated during the conversion reaction based on conversion of $C_{2+}$ hydrocarbons. It is noted that the "feed" to the conversion reaction can correspond to the effluent from a prior conversion stage where a conventional conversion catalyst was used. In such aspects, a natural gas feedstock can first be exposed to a conventional conversion catalyst, to take advantage of the improved aromatics selectivity and decreased methane selectivity provided by those conversion catalysts. The resulting first stage effluent, including any unreacted ethane, can then be exposed to a second stage catalyst corresponding to the catalyst specified herein in order to decrease or minimize the ethane content.

In aspects involving multiple conversion stages, it is noted that the conversion products in the first stage effluent can include aromatics and hydrogen, typically as molecular hydrogen. Conventionally, it would be expected that including both hydrogen and aromatics in the feed into the second stage would result in an undesirable amount of hydrogenation of the aromatics in the presence of the second stage catalyst. It has been unexpectedly discovered, however, that in comparison with conventional catalysts, the specified catalyst has an increased selectivity for converting ethane to methane with decreased selectivity for the hydrogenation of aromatics present in the feed with the methane, ethane, and molecular hydrogen.

Additionally or alternatively, in various aspects a molar ratio of $C_3$ hydrocarbons and/or $C_4$ hydrocarbons in a converted product stream to $C_3$ and/or $C_4$ hydrocarbons in the feed stream can be 0.15 or less, or 0.10 or less, or 0.05 or less, such as down to 0.001 or possibly still lower. This can represent the substantially complete conversion of $C_3$ and/or $C_4$ hydrocarbons (to form methane or aromatics) that can occur during the conversion reaction. It should be noted, however, that when a first catalytic stage is used, it is typically operated to convert ≥50 mole % of $C_{3+}$ paraffin in the feed to the first stage, e.g., ≥75 mole %, such as ≥90 mole %, or ≥95 mole %.

In certain aspects, the source of the methane-containing feed can include natural gas, e.g., raw natural gas ("raw gas"). Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more of petroleum deposits, coal deposits, and shale deposits. The natural gas can be obtained by conventional production methods but the invention is not limited thereto. Raw natural gas is a natural gas obtained from a geologic formation without intervening processing, except for (i) treatments to remove impurities such as water and/or any other liquids, mercaptans, hydrogen sulfide, carbon dioxide; and (ii) vapor-liquid separation, e.g., for adjusting the relative amounts of hydrocarbon compounds (particularly the relative amounts of $C_{4+}$ hydrocarbon compounds) in the natural gas; but not including (iii) fractionation with reflux. Conventional methods can be used for removing impurities and/or adjusting the relative amount of hydrocarbon compounds present in the feedstock, but the invention is not limited thereto. One suitable raw natural gas comprises 3 mole % to 70 mole % methane, 10 mole % to 50 mole % ethane, 10 mole % to 40 mole % propane, and 5 mole % to 40 mole % butanes and 1 mole % to 10 mole % of total $C_5$ to $C_9$ hydrocarbon. In certain aspects, ≥50 wt. % of the feedstock comprises natural gas, such as raw natural gas, e.g., ≥75 wt. %, or ≥90 wt. %, or ≥95 wt. %.

Any form of raw gas can be used as a source material, although the raw gas is typically one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |
| $CH_4$ | 0-80 (64.48) | 0-97 (91.01) | 0-98 (94.87) |
| $C_2H_6$ | 5-20 (11.98) | 2-10 (4.88) | 1-5 (2.89) |
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.1-1 (0.09) |

In certain aspects, the feedstock comprises ≥75 wt. % Associated Gas, based on the weight of the feedstock, e.g., ≥90 wt. %, or ≥95 wt. %. Associated Gas is typically found with petroleum deposits, e.g., dissolved in the oil or as a free "gas cap" above the oil in a reservoir. In conventional petroleum production, the lack of effective natural transportation facilities, e.g., the lack of natural gas liquefaction and/or pipeline facilities, can result in Associated Gas being stranded at or near the reservoir. This in turn can lead to a need for undesirable natural gas flaring. As an example, the conversion catalyst and methods of using a conversion catalyst as described herein can be advantageous in remote or under-developed locations, where (i) the lack of cryogenic methane separation facilities limits the utility of conventional natural gas aromatization processes and/or (ii) Associated Gas remains stranded at a remote location for failure to meet one or more specifications of an available pipeline. Small scale plants using a catalyst as described herein could allow effective recovery of these light hydrocarbon resources as liquid hydrocarbons and/or transport of the light hydrocarbon resources via pipeline. In such aspects, the feedstock can comprise ethane in an amount ≥1 wt. %, e.g., ≥5 wt. %, such as ≥10 wt. %, and possibly up to 25 wt. % or more.

Aspects of the invention which include contacting a feed containing methane and ethane with the conversion catalyst described herein to produce aromatics (such as naphtha, BTX, etc.) and/or methane will now be described in more detail. The invention is not limited to these aspects, and this description is not meant to foreclose other aspects within the broader scope of the invention.

Definitions

The term "aromatic hydrocarbons" refers to molecules containing one or more aromatic rings. Examples of aromatic hydrocarbons are benzene, toluene, xylenes, naphthalene, and methylnaphthalenes.

The term "aromatic" refers to unsaturated compounds with at least one closed ring of at least 6 atoms, with all of the ring atoms being co-planar or almost co-planar and covalently linked, and with all of the ring atoms being part of a mesomeric system. As used herein, when the "aromatic" substituent is monocyclic, it preferably contains 6 ring atoms, and when the "aromatic" substituent is polycyclic, it preferably contains 10 ring atoms contained in fused rings.

The term "Ce" hydrocarbon refers to a hydrocarbon with "n" carbon atoms, "$C_n$-$C_m$ hydrocarbons" represents hydrocarbons having between "n" and "m" carbon atoms, and "$C_{n+}$ hydrocarbons" represents hydrocarbons having n or more carbon atoms. The term "$C_n$" aromatic refers to an aromatic hydrocarbon with "n" carbon atoms, "$C_n$-$C_m$ aromatics" represents aromatic hydrocarbon having between "n" and "m" carbon atoms, and "$C_{n+}$ aromatics" represents aromatic hydrocarbons having n or more carbon atoms. It is noted that toluene corresponds to a $C_7$ aromatic.

The term "catalyst" refers to a material, which under certain conditions of temperature or pressure increases the rate of specific chemical reactions. A catalyst may also be a material that performs as a physisorbent or chemisorbent for specific components of the feed stream.

The term "chain length" may broadly refer to a number of atoms forming and/or making a backbone and/or structure of a molecule and/or compound, such as carbon atoms for a hydrocarbon.

The term "chemical reaction" refers to any process including the breaking or making of chemical bonds including a dissociation, recombination, or rearrangement of atoms.

The term "crude oil" refers to hydrocarbons formed primarily of carbon and hydrogen atoms. The hydrocarbons may also include other elements, such as, but not limited to, halogens, metallic elements, nitrogen, oxygen, or sulfur. Hydrocarbons derived from an oil-bearing formation may include, but are not limited to, kerogen, bitumen, pyrobitumen, asphaltenes, resins, oils, or combinations thereof.

The term "fixed-bed reactor" refers to a reactor containing catalyst material typically in pellet form, packed in a static bed.

The term "higher hydrocarbons" refers to hydrocarbon(s) having more than one carbon atom per molecule, oxygenate having at least one carbon atom per molecule, e.g., ethane, ethylene, propane, propylene, benzene, toluene, xylenes, naphthalene, and/or methyl naphthalene; and/or organic compound(s) including at least one carbon atom and at least one non-hydrogen atom, e.g., methanol, ethanol, methylamine, and/or ethylamine.

The term "hydrocarbon" refers to an organic compound that includes primarily, if not exclusively, the elements hydrogen and carbon. Hydrocarbons may also include other elements, such as, but not limited to, halogens, metallic elements, nitrogen, oxygen, and/or sulfur. Hydrocarbons generally fall into two classes: aliphatic, or straight chain hydrocarbons, and cyclic, or closed ring hydrocarbons, including cyclic terpenes. Examples of hydrocarbon-containing materials include any form of natural gas, oil, coal, and bitumen.

The term "hydrocarbon stream" refers to a hydrocarbon or mixtures of hydrocarbons that are gases or liquids. For example, hydrocarbon fluids may include a hydrocarbon or mixtures of hydrocarbons that are gases or liquids at formation conditions, at processing conditions or at ambient conditions (15° C. and 1 atm pressure). Hydrocarbon fluids may include, for example, oil, natural gas, coalbed methane, shale oil, pyrolysis oil, pyrolysis gas, a pyrolysis product of coal, and other hydrocarbons that are in a gaseous or liquid state The term "natural gas" refers to a multi-component gas obtained from a crude oil well (associated gas) or from a subterranean gas-bearing formation (non-associated gas). The composition and pressure of natural gas can vary significantly. A typical natural gas stream contains methane ($C_1$) as a significant component. Raw natural gas may also contain ethane (C$_2$), higher molecular weight hydrocarbons, acid gases (such as carbon dioxide, hydrogen sulfide, carbonyl sulfide, carbon disulfide, and mercaptans), and minor amounts of contaminants such as water, nitrogen, iron sulfide, wax, and crude oil. As used herein, natural gas includes gas resulting from the regasification of a liquefied natural gas, which has been purified to remove contaminates, such as water, acid gases, and most of the higher molecular weight hydrocarbons.

The term "high quality gas" refers to a gas that has undergone natural gas processing to separate various hydrocarbons and fluids from a raw natural gas. Also referred to as pipeline quality dry natural gas.

The term "raw natural gas" refers to a gas that is included of methane, but may also include numerous other light hydrocarbons including ethane, propane, and butanes. Higher molecular weight hydrocarbons, including pentanes, hexanes, and impurities like benzene may also be present in small amounts. Furthermore, raw natural gas may contain amounts of non-hydrocarbon impurities, such as nitrogen, hydrogen sulfide, carbon dioxide, and traces of helium, carbonyl sulfide, various mercaptans, and water.

The term "zeolite" is defined to refer to a crystalline material having a porous framework structure built from tetrahedra atoms connected by bridging oxygen atoms. Examples of known zeolite frameworks are given in the "Atlas of Zeolite Frameworks" published on behalf of the Structure Commission of the International Zeolite Association", 6$^{th}$ revised edition, Ch. Baerlocher, L. B. McCusker, D. H. Olson, eds., Elsevier, New York (2007) and the corresponding web site, http://www.iza-structure.org/databases/. Under this definition, a zeolite can refer to aluminosilicates having a zeolitic framework type as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework.

The term "oil and gas reservoir" refers to a well or reservoir that is a subsurface zone that produces oil and/or gas and lacks communication other reservoirs. As used in the claims, "oil and gas well" and "oil and gas reservoir" are interchangeable.

The term "reservoir" refers to a formation or a portion of a formation that includes sufficient permeability and porosity to hold and transmit fluids, such as hydrocarbons or water.

Conversion Catalyst and Conversion Conditions

In various aspects, the specified conversion catalyst includes a crystalline material having zeolitic framework structure material and one or more metals with dehydrogenation activity supported on the catalyst. In particular, the one or more metals with dehydrogenation activity can correspond to a combination of Zn with Mo, or Zn with one or more of Mo, Fe, and Pt. For example, the conversion catalyst can include 10 wt. % or more of a zeolite or other crystalline material having a zeolitic framework structure and 0.05 wt. % or more of a dehydrogenation component. When the zeolitic material and dehydrogenation component together comprise less than 100 wt. % of the catalyst, 90 wt. % or more of the remainder of the catalyst can comprise a binder or other matrix component, such as wt. % or more.

In some aspects, the catalyst can include 20 wt. % or more of the crystalline material having a zeolitic framework structure, based on the weight of the catalyst, or 25 wt. % or more, such as in the range of from 30 wt. % to 99.9 wt. %. The crystalline material can correspond to any convenient composition suitable for forming a zeolitic framework structure, such as a zeolitic framework structure corresponding to an un-substituted aluminosilicate, a substituted aluminosilicate, or a combination thereof.

The zeolitic portion of a catalyst can typically include 90 wt. % or more of one or more specified framework structures, or 95 wt. % or more. The zeolitic material can be one that is in hydrogen form, e.g., one that has been synthesized in the alkali metal form, but is then converted from the alkali to the hydrogen form. Typically the zeolitic material is one having a medium pore size and a Constraint Index of 2-12 (as defined in U.S. Pat. No. 4,016,218). Examples of suitable zeolites (zeolitic framework structures) include ZSM-5 (MFI), ZSM-11 (MEL), ZSM-12 (MTW), ZSM-22 (TON), ZSM-23 (MTT), ZSM-35 (FER), ZSM-48 (MRE), including and mixtures and intermediates thereof such as ZSM-5/ZSM-11 admixture. Optionally, the zeolitic material is one comprising at least one set of pores of substantially uniform size extending through the framework structure, wherein geometric mean of the cross-sectional dimensions of each of the sets of pores is >5 Å, or >5.3 Å, e.g., ≥5.4 Å such as ≥5.5 Å, or in the range of 5 Å to 7 Å, or 5.4 Å to 7 Å. ZSM-5 and/or ZSM-12 are suitable, particularly H-ZSM-5. In certain aspects, the molecular sieve has a relatively small crystal size, e.g., small crystal ZSM-5, meaning ZSM-5 having a crystal size ≤0.05 μm, such as in the range of 0.02 μm to 0.05 μm. Small crystal ZSM-5 and the method for determining molecular sieve crystal size are disclosed in U.S. Pat. No. 6,670,517, which is incorporated by reference herein in its entirety.

When the molecular sieve component comprises at least one aluminosilicate, e.g., at least one zeolite, the aluminosilicate's silica:alumina ratio (substantially the same as the aluminosilicate's Si:Al$_2$ atomic ratio) is typically ≥2, e.g., in the range of from 5 to 100. The silica:alumina ratio is meant to represent the Si:Al$_2$ atomic ratio in the rigid anionic framework structure of the crystalline aluminosilicate. In other words, aluminum in (i) any matrix or hinder or (ii) in cationic or other form within the crystalline aluminosilicate's channels is excluded from the silica alumina ratio. Alternatively or in addition, the catalyst can be made more resistant to deactivation (and increase aromatic hydrocarbon yield) by including phosphorous with the molecular sieve component. Conventional methods can be utilized for adding phosphorous, but the invention is not limited thereto. When used, the amount of phosphorous is typically ≥1 wt. % based on the weight of the molecular sieve component. For example, when the molecular sieve component comprises aluminosilicate, the phosphorous:aluminum atomic ratio can be in the range of from 0.01 to 1. Zeolite having a higher silica:alumina ratio can be utilized when a lower catalyst acidity is desired, e.g., in the range of from 44 to 100, such as from 50 to 80, or 55 to 75.

In addition to the zeolitic framework structure component, the catalyst can include 0.1 wt. % or more, based on the weight of the catalyst, of a dehydrogenation component comprising Zn and further comprising one or more of Mo, Pt, and Fe. In some aspects, the dehydrogenation component is Zn and Mo. The amount of dehydrogenation component can correspond to 0.1 wt. % to 10 wt. %, based on the weight of the catalyst, or 0.1 wt. % to 5.0 wt. %, or 0.5 wt. % to 2.0 wt. %. In various aspects, the weight ratio of Zn to the other metal(s) in the dehydrogenation component can be 1.0 or more, or 1.5 or more, or 2.0 or more, or 3.0 or more, such as up to 10 or possibly still higher.

In various aspects, the catalyst can further comprise an optional matrix component, e.g., one or more inorganic binders. A matrix component can be used, e.g., to make the catalyst more resistant to the temperatures and other conditions employed in the conversion reaction. The amount of matrix component is not critical. When present, the amount of matrix component is typically in the range of 0.01 times the weight of the zeolitic framework structure material to about 0.9 times the weight of the zeolitic material, e.g., in the range of 0.02 to 0.8. The matrix component can include active materials, such as synthetic or naturally occurring zeolites. Alternatively, or in addition, the matrix component can include clays and/or oxides such as alumina, silica, silica-alumina, zirconia, titania, magnesia or mixtures of these and other oxides. The matrix component can include naturally occurring materials and/or materials in the form of gelatinous precipitates or gels including mixtures of silica and metal oxides. Clays may also be included with the oxide type binders to modify the mechanical properties of the catalyst or to assist in its manufacture. Alternatively or in addition, the matrix component can include one or more substantially inactive materials. Inactive materials suitably serve as diluents to control the amount of conversion so that products may be obtained economically and orderly without employing other means for controlling the rate of reaction. Alternatively or in addition to any phosphorous added to or impregnated into the molecular sieve component, the matrix component can optionally include phosphorous, e.g., to lessen catalyst acidity. The matrix component is optional.

The catalyst can be one that has been subjected to one or more treatments, e.g., a selectivation treatment to increase selectivity for producing desired aromatic hydrocarbon compounds such as para-xylene. For example, the selectivation can be carried out before introduction of the catalyst into the reactor and/or in-situ in the reactor, e.g., by contacting (optionally a plurality of times) the catalyst with a selectivating agent, such as at least one organosilicon in a liquid carrier and subsequently calcining the catalyst at a temperature of 350 to 550° C. Such a selectivation process is described in detail in U.S. Pat. Nos. 5,633,417 and 5,675,047, which are incorporated by reference herein in their entirety.

Typically, the catalyst has a surface area as measured by nitrogen physisorption in the range of from 100 m$^2$/g to 600 m$^2$/g, e.g., in the range of from 200 m$^2$/g to 500 m$^2$/g. When the catalyst comprises aluminosilicate which includes phosphorous, the phosphorous:aluminum atomic ratio is typically in the range of from 0.01 to 0.5. For example, the catalyst can contain ≥10 wt. % of phosphorous-modified alumina, such as ≥15 wt. %, or in the range of from 10 wt. % to 20 wt. %.

The conversion reaction can be performed by exposing a feed to at least one of the specified conversion catalysts, which is typically located in at least one bed within a conversion reaction zone. Conventional fixed, moving, and/or fluidized beds can be used in the reaction zone, but the invention is not limited thereto.

During conversion, at least a portion of a feed comprising methane and $C_2$ hydrocarbon (e.g., ethane) is exposed to a catalytically effective amount of the specified catalyst under conditions that are effective for selectively converting at least a portion of the feed to methane with lesser selectivity to aromatic hydrocarbon, e.g., 1% less (weight basis) than the methane selectivity, such as 5% less, or 10% less, or 25% less, or 50% less, or more. Aromatics yield from $C_2$ hydrocarbon conversion is significantly less that as would result from the use of the conventional aromatization catalyst (e.g., one that contains substantially the same amount of Zn but without Mo, Pt, or Fe) with substantially the same feed and under substantially the same conditions, e.g., 5% less (weight basis), such as 10% less, or 25% less, or 50% less, or 75% less.

In certain aspects, a feed comprising methane and $C_2$ hydrocarbon is exposed to the specified catalyst under conversion conditions that include a temperature in the range of from 400° C. to 850° C., such as 750° C. to 850° C., or 400° C. to 700° C., a pressure in the range of from about 0.7 bar-a (~70 kPa-a) to about 4 bar-a (400 kPa-a), or about 1 bar-a (~100 kPa-a) to about 4 bar-a (400 kPa-a), and/or a space velocity (WHSV) ≥0.1 hr$^{-1}$. In some aspects, the temperature is in the range of from 500° C. to 675° C., the pressure is in the range of from about 0.7 bar-a (~70 kPa-a) to about 2.5 bar-a (~250 kPa-a), and the weight hourly space velocity (WHSV) is in the range of from 0.1 hr$^{-1}$ to 20 hr$^{-1}$, e.g. 0.2 hr$^{-1}$ to 5 hr$^{-1}$.

In some aspects, a two-stage (or other multi-stage) configuration can be used where a second catalytic conversion stage (or other later stage) of the configuration includes the specified catalyst. In such aspects, the conversion catalyst of the first stage can correspond to a conventional catalyst (i.e., not the specified catalyst) for conversion of the $C_{2+}$ components, and particularly the $C_{3+}$ components, in a natural gas stream and/or other methane-containing stream into heavier hydrocarbons. Examples of such conventional catalysts can include medium pore molecular sieves with one or more active metals. Examples of suitable molecular sieves includes materials with zeolitic framework structures corresponding to the group consisting of a MCM-22 family material, ZSM-5, ZSM-11, ZSM-12, ZSM-21, ZSM-22, ZSM-23, ZSM-35, ZSM-38, ZSM-48, ZSM-50, ZSM-57, MCM-68 and mixtures of two or more thereof. Preferably, the aluminosilicate is ZSM-11 or H-ZSM-11 (the acidic form of ZSM-11), and more preferably, the aluminosilicate is ZSM-5 or H-ZSM-5 (the acidic form of ZSM-5). Examples of suitable active metals can include Zn, Ga, and combinations thereof. In such aspects, a suitable conversion catalyst can correspond to the catalyst described in U.S. application Ser. No. 15/469,725, corresponding to U.S. Patent Application Publication No. 2017/0305812, which is incorporated herein by reference for the limited purpose of describing a suitable catalyst for the first stage of a multi-stage configuration.

In such a two-stage (or other multi-stage) configuration, a suitable feed to the initial stage can be a natural gas feed, such as a raw gas feed and/or Associated Gas feed, as described above. The feed can be conducted to the first catalytic conversion stage without first removing methane and/or ethane from the feed. Suitable conversion conditions can include exposing the feed to the first stage (conventional) catalyst at a temperature in the range of from 400° C. to 700° C., and a pressure in the range of from 35 kPa to 2200 kPa, e.g., 35 kPa to 1480 kPa. Typically, the process conditions further include a weight hourly space velocity (WHSV) ≥0.1 hr$^{-1}$. More typically, the conditions include introducing the feedstock into a reaction zone which has been heated to a temperature in a range of from 400° C. to 630° C., and has a pressure in the range of from about 138 kPa (20 psia) to about 2070 kPa (300 psia), such as a temperature in the range of from 500° C. to 625° C. and a pressure in the range of from 30 psia (207 kPa) to 80 psia (522 kPa). WHSV can be in the range of from 0.1 hr$^{-1}$ to 20 hr$^{-1}$. More typically, the temperature is in the range of from 450° C. to 605° C., the pressure is in the range of from about 207 kPa (30 psia) to about 522 kPa (80 psia), and the weight hourly space velocity (WHSV) is in the range of from 0.1 to 10 hr$^{-1}$. Typically, the WHSV of $C_{2+}$ hydrocarbon (the "$C_{2+}$ WHSV") in the specified aromatization feed with respect to the catalyst is in the range of from 0.1 hr$^{-1}$ to 20 hr$^{-1}$, e.g., 0.2 hr$^{-1}$ to 5 hr$^{-1}$, or 0.3 hr$^{-1}$ to 1 hr$^{-1}$. The $C_{2+}$ WHSV is the hourly rate of the $C_{2+}$ hydrocarbon (in grams per hour) exposed to the catalyst per gram of the catalyst. The reaction is typically endothermic. Generally, the average temperature drop across the reaction zone is ≤600° C., more typically in the range of from 20° C. to 200° C., e.g., in the range of from 50° C. to 150° C.

It is noted that the conversion conditions and conversion catalyst in a first stage can generate a first stage effluent that includes hydrogen. In some optional aspects, this hydrogen can be at least partially removed from the first stage effluent prior to introducing a remaining portion of the first stage effluent into the second stage. In other aspects, the hydrogen can be retained in the portion of the first stage effluent that is introduced into the second stage. It has been unexpectedly discovered that this hydrogen from the first stage effluent can be beneficial for improving the activity of the second stage catalyst (i.e., a catalyst as described herein) for conversion of ethane to methane and optionally additional aromatics over those produced in the first Aromatics (and/or other heavier hydrocarbons) produced from the $C_{2+}$ components of the feed to the first stage, are generally from the $C_{3+}$ components. Depending on the aspect, the aromatics and/or other heavier hydrocarbons can be separated from the first stage effluent prior to processing in the second stage, or the aromatics and/or other heavier hydrocarbons can remain as part of the input to the second stage.

In some aspects, it can be beneficial to operate a multi-stage conversion reaction with the first stage at a pressure $P_1$ that is higher than a pressure $P_2$ for the second stage. In such aspects, the pressure in the second stage can be less than the pressure in the first stage, e.g., $P_2 \leq 0.95 \cdot P_1$, such as $P_2 \leq 0.90 \cdot P_1$, or $P_2 \leq 0.85 \cdot P_1$, or $P_2 \leq 0.80 \cdot P_1$. Optionally, the temperature $T_1$ of the first stage can be lower than the temperature $T_2$ for the second stage, such as $T_1 \leq 0.90 \cdot T_2$, e.g., $T_1 \leq 0.85 \cdot T_2$, such as $T_1 \leq 0.80 \cdot T_2$.

Example of Natural Gas Processing System Configuration

FIG. 1 shows an example of a process flow for processing a natural gas stream to remove impurities and/or reduce the content of $C_{2+}$ hydrocarbons while also producing additional $C_{6+}$ hydrocarbons. In the example shown in FIG. 1, the process flow is located at an extraction site, such as a well reservoir. Prior to exposing the natural gas stream to a catalyst as described herein, the natural gas stream can be processed in one or more processing steps to reduce or minimize the amount of impurities in the stream.

As shown in FIG. 1, a raw hydrocarbon flow or stream 202, such as a stream produced from a reservoir, can flow into a production separator 204. In some embodiments, the raw hydrocarbon stream 202 may contain crude oil and raw natural gas along with water, trace organic compounds, trace metals, and other entrained liquids and solids. A crude oil stream 206 can be taken from the bottom of the separator 204. The crude oil stream 206 can be directed to a field crude stabilizer 208, where water, light hydrocarbons, and gas contaminants are boiled off to produce a stabilized crude oil liquid stream 210. As shown in FIG. 1, an overhead gas stream 212 from the field crude stabilizer 208 may be combined with a raw natural gas stream 214 taken from the top of the separator 204 to form a combined stream 216. In various embodiments, the raw natural gas stream 214 may include methane, ethane, propane, butanes, nitrogen, carbon dioxide, and hydrogen, among other components. In some examples, the overhead gas stream 212 and/or the raw natural gas stream 214 may include sulfur compounds, such as mercaptans, sulfides, and other organosulfur compounds, in addition to hydrogen sulfide ($H_2S$). Alternatively, a reservoir that contains primarily gas phase hydrocarbons can produce a raw natural gas stream 214 without requiring separation from other heavier hydrocarbons. In such alternative aspects, stream 216 can correspond to at least a portion of the raw natural gas stream 214.

In some aspects, the (combined) stream 216 can include 10 wt. % or more of ethane, relative to a weight of hydrocarbons in the stream, or 15 wt. % or more, or 18 wt. % or more, or 20 wt. % or more.

If stream 216 contains organosulfur compounds, $H_2S$, or both, the stream 216 may optionally be treated in a sulfur removal stage 230 to produce a sweetened stream 235 containing a reduced or minimized content of organosulfur compounds and/or $H_2S$. The sulfur-containing compounds can be at least partially removed by an adsorption column, a Claus process, a counter-current separation column, or any number of other techniques. One example of a suitable process can be a sweetening process such as an amine separation process. Such a sweetening process can be effective for removal of both $H_2S$ and $CO_2$. The separated $H_2S$ and/or $CO_2$ stream 232 can undergo any convenient type of further processing, if desired.

The sweetened gas stream may then optionally be treated in a dehydration stage 240 to remove water 242 in order to produce a dehydrated stream 245 having a reduced or minimized content of water. The water removal can be performed by any convenient method, such as by adsorption, absorption, and/or exposing the stream to a liquid medium that selectively retains the water as the stream passes through the medium.

The dehydrated stream 245 can then be exposed to at least the specified catalyst for conversion of $C_{2+}$ hydrocarbons into $C_{6+}$ hydrocarbons and methane in a conversion stage 250. Exposing the dehydrated stream 245 to the conversion catalyst under effective conversion conditions in the conversion stage 250 can decrease or minimize the content of $C_2$, $C_3$, and $C_4$ compounds in the resulting conversion product 255 while producing additional methane and $C_{6+}$ hydrocarbons, such as $C_{6+}$ aromatics. It is noted that the content of $C_{6+}$ hydrocarbons in the dehydrated stream 245 is expected to be low; if the original hydrocarbon stream 202 from the reservoir contains a meaningful amount of $C_{5+}$ compounds or $C_{6+}$ compounds, it is likely that the stream 202 would be passed through a production separator 204 to separate such heavier compounds from the $C_{4-}$ hydrocarbons.

In some aspects, a plurality of conversion stages 250 can be included, with at least a portion of the effluent from a first conversion stage (containing at least methane and ethane) being used as the input for a second conversion stage. In such aspects, a conventional conversion catalyst can be used in the first stage and a catalyst as described herein (the specified catalyst) can be used in the second stage. The second stage selectively converts ethane to methane with less selectivity for aromatics than the selectivity for converting paraffin to aromatics in the first stage, e.g., at least 1% less, such as at least 5% less, or at least 10% less, or at least 25% less, or at least 50% less, or at least 75% less.

The resulting conversion product 255 can then be passed through one or more separation stages to separate the conversion product into desired output streams. For example, a first separation stage 260 can be used to separate out a $C_{5+}$ stream 262 (such as an output stream including benzene, toluene, and xylenes) from a remaining portion 265 of the conversion product. A second separation stage 270, such as a cold box, can be used to separate any remaining $C_{2+}$ hydrocarbons 272 from a methane-containing stream 275. A membrane separator 280 (or another type of hydrogen separator) can then be used to separate a hydrogen-containing stream 282 from a methane product stream 285. In some aspects, the methane product stream can have a suitable energy content for pipeline transport. Additionally or alternatively, the ethane content in the methane product stream can correspond to 12 wt. % or less relative to a weight of hydrocarbons in the stream, or 10 wt. % or less. Optionally, if further reduction of ethane content is desired, an additional optional separation stage 280 can be included prior to membrane separator 270. The additional optional separation stage 280 can correspond to, for example, a cold box for separation of an ethane and/or propane stream 282 from the methane-containing stream 265.

The block diagram of FIG. 1 is not intended to indicate that the gas processing system is required to include all of the components shown in FIG. 1. Further, any number of additional components may be included within the method of producing a higher molecular weight hydrocarbons product. The system may include any suitable types of heaters, chillers, condensers, pumps, compressors, other types of separation and/or fractionation equipment, among others. It is noted that the conversion stage 250 is in fluid communication with the separator 204 via the various intervening components shown in FIG. 1. For example, in a configuration where a plurality of conversion stages 250 are present, a first conversion stage can have a first stage inlet that is in fluid communication with the separator 204. A first stage outlet can be in fluid communication with a second stage inlet. It is further noted that the various types of connectivity shown in FIG. 1 can represent fluid communication between the various components.

Example 1—Catalyst Examples

A series of catalysts including H-ZSM-5 as a crystalline framework structure were produced with various supported metals. The ZSM-5 catalyst contained ~65 wt. % ZSM-5 and ~35 wt. % alumina binder.

The H-ZSM-5 was then used to form catalysts with 1 wt. % Zn supported on the catalyst. As an example, 70 g of the H-ZSM-5 crystals (or grinded alumina-bound H-ZSM-5 catalyst) was dispersed in 400 ml of a solution of Zn-nitrate (3% of $Zn(NO_3)_2$) and stirred for 4 hr at room temperature. The solid, corresponding to Zn-ZSM-5, was recovered and dried at 120° C. for 16 hr.

After forming the Zn-ZSM-5, additional metals could be added to form catalysts with two or more metals. For example, 0.5 wt. % Mo-1.0 wt. % Zn-ZSM-5 could be formed by the following procedure. After recovery and drying of the Zn-ZSM-5, 35 g of dried material was dispersed in a 200 ml of a Molybdenum salt solution (1% of $Mo(NO_3)_3$) and stirred for 4 hr. The solid, corresponding to 0.5 wt. % Mo-1.0 wt. % Zn-ZSM-5, was recovered and dried at 120° C. for 16 hr. A similar procedure was used to form other catalysts, including catalysts with the following combinations of metals: Cu—Zn, La—Zn, Ag—Zn, and Sn—Zn.

Example 2—Conversion Examples

A series of catalysts were used in a high-throughput test reactor for conversion of a model first stage effluent. The model first stage effluent was intended to be representative of a first stage effluent that would be produced from processing of a "rich" natural gas stream in the presence of a first stage (conventional) conversion catalyst. The model first stage effluent used as a feed included methane, ethane, propane, and $H_2$. The molar ratio of methane:ethane:propane:$H_2$ was 50:20:5:25. These ratios reflect the reduced or minimized amount of $C_{3+}$ hydrocarbons that would be expected in a first stage effluent, due to the substantially complete conversion of $C_{3+}$ compounds that can be achieved using a conventional conversion catalyst. The feed was exposed to each catalyst at a WHSV of 0.5 $hr^{-1}$, a temperature of 575° C. or 600° C., and a pressure of 100 kPa-a to 400 kPa-a. The catalysts used included a H-ZSM-S catalyst, 4 different versions of 1.0 wt. % Zn-ZSM-5, and various catalysts corresponding to 0.5 wt. % X-1.0 wt. % Zn-ZSM-5, where X corresponds to Mo, Cu, La, Ag, and Sn.

Figure 2:
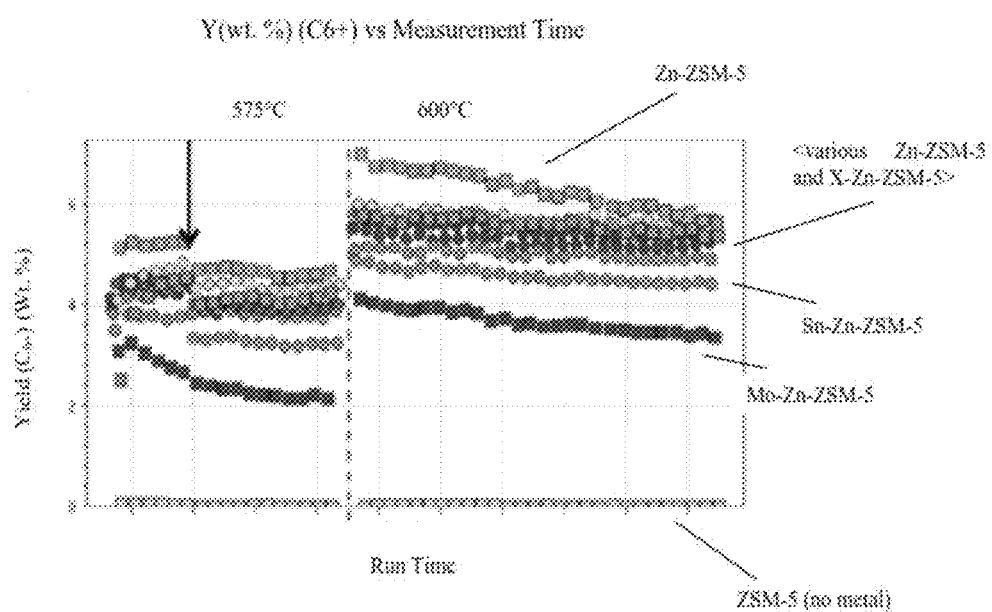
FIG. 2 shows yields of $C_{6+}$ hydrocarbons during processing of a natural gas stream in the presence of various catalysts.

FIG. 2 shows the yield versus time of $C_{6+}$ aromatics generated during exposure of the feed to the various catalysts. The data shown in FIG. 2 (and more generally in FIGS. 3-5 which have the same x-axis as FIG. 2) corresponds to data collected over the course of roughly five days. As indicated by the vertical arrow in FIG. 2, a flow calibration adjustment was made after roughly the first day. This change in flow rate resulted in a modest change in some quantitative values, but otherwise did not impact the general nature of the results. The feed was initially exposed to the catalysts at 575° C., with the temperature being increased to 600° C. during the run as shown in FIG. 2 (and in FIG. 3-5).

The data in FIG. 2 includes results from a large number of catalysts, but the results from most of the catalysts investigated were qualitatively similar. The plurality of catalysts that generated these similar results are indicated generally in FIG. 2 by the arrow labeled "various Zn-ZSM-5 and X—Zn-ZSM-5". For the results that are separately labeled, it is noted that one of the Zn-ZSM-5 catalysts provided a somewhat higher $C_{6+}$ aromatics yield. The yields from this catalyst correspond to the top-most series of data shown in FIG. 2. This particular Zn-ZSM-5 catalyst otherwise provided results similar to the other Zn-ZSM-5 catalysts, and therefore is not separately identified in FIGS. 3-5. Another separately labeled result corresponds to the data for the Sn—Zn-ZSM-5 catalyst. The Sn—Zn-ZSM-5 catalyst produced a somewhat lower yield of $C_{6+}$ aromatics. A still lower yield of $C_{6+}$ aromatics was generated by the Mo—Zn-ZSM-5 catalyst. The results from the Mo—Zn-ZSM-5 catalyst correspond to the data series below the Sn—Zn-ZSM-5 series. The catalyst corresponding to H-ZSM-5 without a supported metal generated substantially no $C_{6+}$ aromatics, as indicated by the bottom series of data.

As shown in FIG. 2, the H-ZSM-5 catalyst resulted in substantially no production of $C_{6+}$ aromatics. The catalysts with Zn supported on the catalyst all resulted in some $C_{6+}$ aromatics production. As shown in FIG. 2, most of the catalysts including Zn as a supported metal resulted in similar aromatics production, with one of the Zn-ZSM-5 catalysts providing slightly higher aromatics production and the Sn—Zn-ZSM-5 catalyst providing slightly reduced aromatics production. The Mo—Zn-ZSM-5 catalyst, however, resulted in lower production of $C_{6+}$ aromatics than any of the other Zn-containing catalysts in FIG. 2. Thus, if viewed solely from the standpoint of activity for aromatics production, the data in FIG. 2 would suggest that supporting both Mo and Zn on a catalyst is a less favorable alternative for conversion of a natural gas feed.

Figure 3:
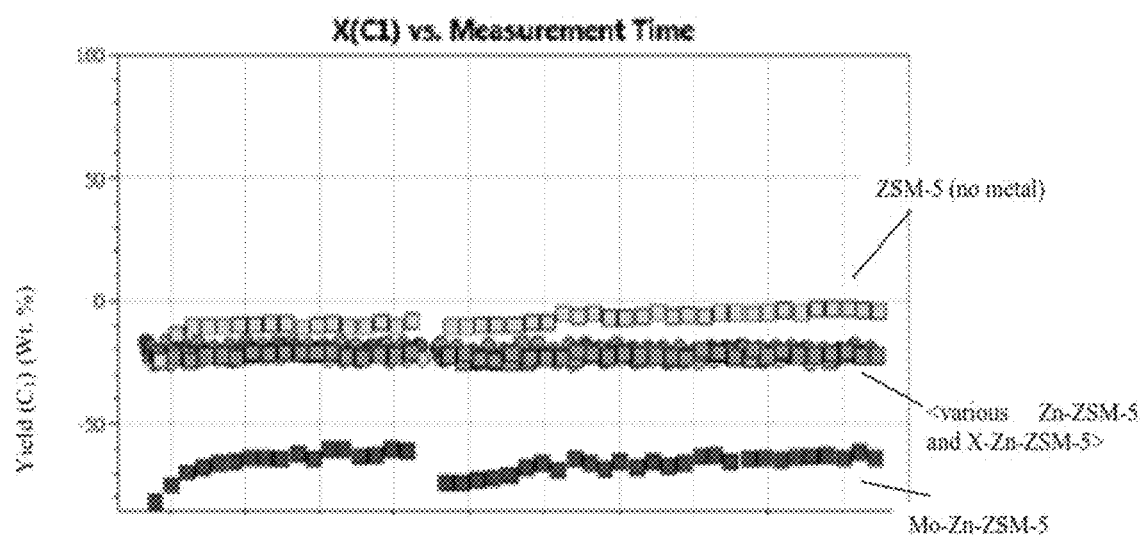
FIG. 3 shows methane conversion results during processing of a natural gas stream in the presence of various catalysts.

Although the Mo—Zn-ZSM-5 catalyst has a relatively low activity for production of $C_{6+}$ aromatics, the Mo—Zn- ZSM-5 has unexpectedly high activity (even in the presence of hydrogen) with respect to other aspects of converting the feed. FIG. 3 shows the amount of methane conversion during the conversion reaction. In FIG. 3, a positive conversion value indicates that the effluent has a lower content of methane than the feed, while a negative conversion value indicates that methane is generated during the conversion reaction. As shown in FIG. 3, the Mo—Zn-ZSM-5 catalyst resulted in an increase in methane content in the product of 60 wt. % or more relative to the methane content of the feed. By contrast, all of the other catalysts including Zn as a supported metal resulted in modest increases in methane content relative to the feed of 10 wt. % to 30 wt. %. It is noted that the Sn—Zn-ZSM-5 catalyst had a similar increase in methane content to the other X—Zn-ZSM-5 catalysts, and therefore is not shown separately. The ZSM-5 without a supported metal provided a still lower increase in methane content of 5 wt. % to 10 wt. %. The results in FIG. 3 demonstrates a substantially increased selectivity for methane formation when performing the conversion reaction in the presence of the Mo—Zn-ZSM-5 catalyst.

Figure 4:
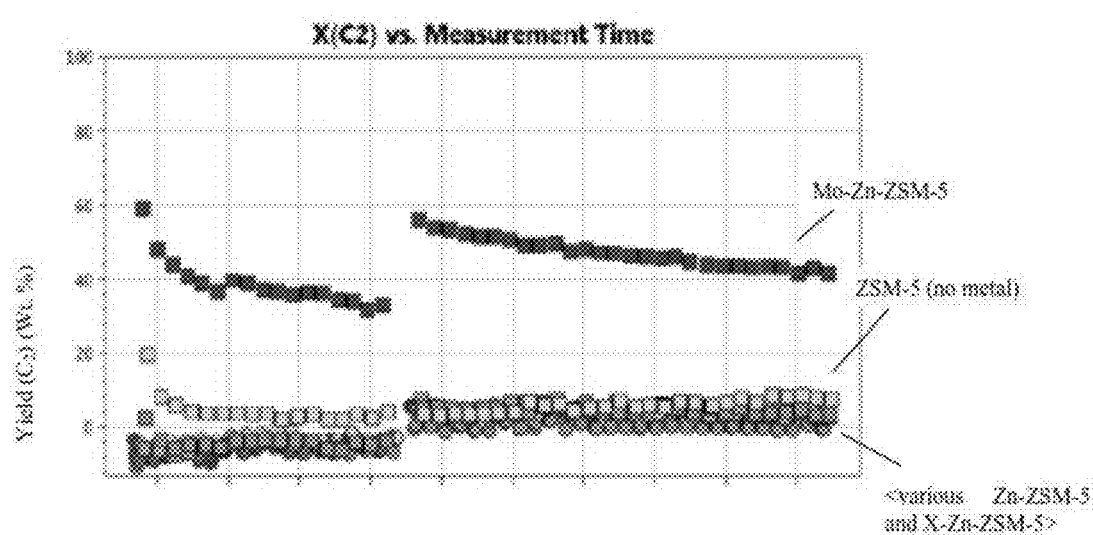
FIG. 4 shows ethane conversion results during processing of a natural gas stream in the presence of various catalysts.

The Mo—Zn-ZSM-5 catalyst also has unexpected activity with regard to ethane conversion. FIG. 4 shows ethane conversion during the conversion reaction. It is noted that the $C_2$ products can correspond to either ethane or ethene. As shown in FIG. 4, exposing the feed to the Mo—Zn-ZSM-5 catalyst resulted in conversion of 40 wt. % or more of the ethane relative to the ethane content of the feed. This is in contrast to the other Zn-containing catalysts in FIG. 4, which had little or no net conversion of ethane under the reaction conditions. In fact, the amount of ethane conversion by the other Zn-containing catalysts was similar to the amount of ethane conversion by the ZSM-5 catalyst that did not included a supported metal. Thus, the data series for the ZSM-5 catalyst (no metal) overlaps with the data series for the various Zn-ZSM-5 and X—Zn-ZSM-5 catalysts. Based on FIG. 4, the Mo—Zn-ZSM-5 catalyst provided unexpected activity for net conversion of ethane under the reaction conditions. Without being bound by any particular theory, this net conversion of ethane is believed to contribute to the unexpected amount of methane produced by the Mo—Zn-ZSM-5 catalyst.

Figure 5:
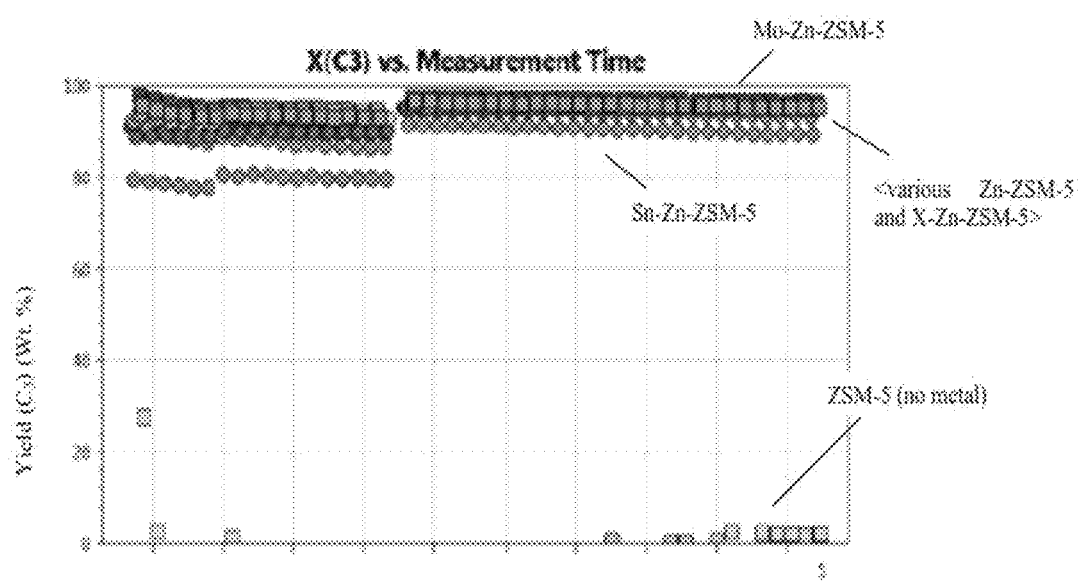
FIG. 5 shows conversion results for conversion of $C_3$ alkanes during processing of a natural gas stream in the presence of various catalysts.

FIG. 5 shows the propane conversion for the various catalysts. As shown in FIG. 5, all but one of the Zn-containing catalysts were effective for substantially complete conversion of the propane in the feed. The Sn—Zn-ZSM-5 catalyst resulted in slightly less than complete conversion of propane, as indicated by the data series located just below the data for the other Zn-ZSM-5 and X-ZSM-5 catalysts. The results for the Mo—Zn-ZSM-5 catalyst were substantially similar the other X—Zn-ZSM-5 catalysts, and therefore overlap with the other data series in FIG. 5.

Based on FIG. 4 and FIG. 5 the Mo—Zn-ZSM-5 catalyst provided unexpectedly superior activity for removal of $C_{2+}$ compounds from the simulated natural gas feed. In a situation where the goal is to create a natural gas stream suitable for pipeline transport, this increased activity for conversion of $C_{2+}$ compounds can reduce, minimize, or possibly eliminate the need to use a cold box separator to remove higher hydrocarbons from the natural gas stream.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method for converting a feed stream, comprising:
separating a hydrocarbon stream to form a raw natural gas stream and a second stream comprising $C_{5+}$ hydrocarbons;
stabilizing the second stream to form a stream comprising liquid hydrocarbons and an overhead gas stream; and
combining at least a portion of the raw natural gas stream with at least a portion of the overhead gas stream to form a combined stream comprising methane and ethane;
exposing a feed stream comprising the combined stream, under effective conversion conditions, to a conversion catalyst comprising a medium pore zeolitic framework structure material and 0.1 wt. % to 10 wt. % of Zn and an additional element comprising one or more of Mo, Pt, and Fe, to form a converted product stream,
wherein a molar ratio of $C_2$ hydrocarbons in the converted product stream to $C_2$ hydrocarbons in the feed stream is 0.8 or less.

2. The method of claim 1, wherein the molar ratio of $C_2$ hydrocarbons in the converted product stream to $C_2$ hydrocarbons in the feed stream is 0.7 or less, and wherein the conversion exhibits a greater selectivity for methane than for aromatics.

3. The method of claim 1, wherein a molar ratio of methane in the converted product stream to the methane in the feed stream is 1.4 or more.

4. The method of claim 1, wherein the feed stream further comprises $C_3$ hydrocarbons, a molar ratio of $C_3$ hydrocarbons in the converted product stream to $C_3$ hydrocarbons in the feed stream being 0.15 or less.

5. The method of claim 1, wherein the feed stream further comprises $C_4$ hydrocarbons, a molar ratio of $C_4$ hydrocarbons in the converted product stream to $C_4$ hydrocarbons in the feed stream being 0.15 or less.

6. The method of claim 1, wherein the converted product stream comprises 1.0 wt. % or more of $C_{6+}$ hydrocarbons, the $C_{6+}$ hydrocarbons optionally comprising $C_{6+}$ aromatics.

7. The method of claim 1, wherein the zeolitic framework structure material comprises an MFI framework structure, a MEL framework structure, a MTW framework structure, a TON framework structure, a MTT framework structure, a FER framework structure, a MRE framework structure, or a combination thereof.

8. The method of claim 1, wherein the zeolitic framework structure material comprises an MFI framework structure, or wherein the zeolitic framework structure material comprises ZSM-5.

9. The method of claim 1, wherein the additional element includes Mo.

10. The method of claim 1, wherein the additional metal is Mo, and the conversion catalyst has a weight ratio of Zn to Mo of 1.5 or more.

11. The method of claim 1, wherein the feed stream comprises at least a portion of a natural gas stream.

12. The method of claim 1, wherein the method further comprises:
passing the combined stream through a sweetening stage to form at least a sweetened combined stream, at least a portion of the sweetened combined stream being used as the feed stream; and
separating from the converted product stream at least a $C_{6+}$ product stream and a methane-containing stream.

13. The method of claim 1, wherein the effective conversion conditions comprise a temperature of 400° C. to 700° C.

14. A method for converting a paraffinic feedstock, comprising:
converting a feedstock comprising paraffin in the presence of a first stage conversion catalyst in a first stage operating under first conversion conditions to form a first stage effluent comprising methane, ethane, and aromatics;
exposing at least a portion of the first stage effluent under second conversion conditions in a second stage to a second conversion catalyst comprising a medium pore zeolitic framework structure material and 0.1 wt. % to 10 wt. % of Zn and one or more of Mo, Pt, and Fe supported on the catalyst, to form a converted product stream,
wherein a molar ratio of $C_2$ hydrocarbons in the converted product stream to $C_2$ hydrocarbons in the feed stream is 0.8 or less.

15. The method of claim 14, wherein the first stage effluent further comprises hydrogen, and/or wherein additional hydrogen is added to the first stage effluent before the second stage.

16. The method of claim 14, wherein the feed stream comprises at least a portion of a natural gas stream.

17. The method of claim 14, wherein the method further comprises:
separating a hydrocarbon stream to form a raw natural gas stream and a second stream comprising $C_{5+}$ hydrocarbons;
stabilizing the second stream to form a stream comprising liquid hydrocarbons and an overhead gas stream; and
combining at least a portion of the raw natural gas stream with at least a portion of the overhead gas stream to form a combined stream, the combined stream comprising the feed stream.

18. The method of claim 14, wherein the method further comprises:
passing the combined stream through a sweetening stage to form at least a sweetened combined stream, at least a portion of the sweetened combined stream being used as the feed stream;
separating from the converted product stream at least a $C_{6+}$ product stream and a methane-containing stream; and
introducing the methane-containing stream into a pipeline.

19. The method of claim 14, wherein the second conversion conditions comprise a temperature of 400° C. to 700° C.

20. The method of claim 14, wherein the first conversion conditions comprise a pressure $P_1$, the second conversion conditions comprise a pressure $P_2$, and $P_2 \leq 0.95 \cdot P_1$.

21. The method of claim 14, wherein the first conversion conditions comprise a pressure $T_1$, the second conversion conditions comprise a pressure $T_2$, and $T_1 \leq 0.90 \cdot T_2$.

22. The method of claim 14, wherein the second conversion catalyst comprises Zn and Mo.

23. A system for converting a feedstock, comprising:
a separation stage for forming a raw natural gas stream and a second stream comprising $C_{5+}$ hydrocarbons from a hydrocarbon stream;
a first stage reactor comprising a first conversion catalyst, a first stage inlet in fluid communication with the separation stage for receiving at least a portion of the raw natural gas stream, and a first stage outlet;
a second stage reactor comprising a second conversion catalyst, a second stage inlet in fluid communication with the first stage outlet, and a second stage outlet, the second conversion catalyst comprising a medium pore zeolitic framework structure material, Mo, and 0.1 wt. % to 10 wt. % of Zn.

* * * * *